(12) United States Patent
Bock et al.

(10) Patent No.: US 8,376,566 B2
(45) Date of Patent: *Feb. 19, 2013

(54) METHOD AND APPARATUS FOR OBJECT VIEWING, OBSERVATION, INSPECTION, IDENTIFICATION, AND VERIFICATION

(76) Inventors: Joel N. Bock, Teaneck, NJ (US); Ronald R. Erickson, Brooklyn, NY (US); Eliezer D. Sandler, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/092,491

(22) Filed: Apr. 22, 2011

(65) Prior Publication Data

US 2011/0261360 A1  Oct. 27, 2011

Related U.S. Application Data

(63) Continuation of application No. 12/048,932, filed on Mar. 14, 2008, now Pat. No. 7,931,384, which is a continuation of application No. 11/298,319, filed on Dec. 8, 2005, now Pat. No. 7,364,317, which is a continuation of application No. 10/756,211, filed on Jan. 12, 2004, now Pat. No. 7,001,038.

(60) Provisional application No. 60/439,368, filed on Jan. 10, 2003.

(51) Int. Cl.
*A47F 11/10* (2006.01)
*G01N 21/00* (2006.01)
(52) U.S. Cl. ............................ 362/125; 362/253; 356/30
(58) Field of Classification Search .................. 362/125, 362/253; 356/30
See application file for complete search history.

(56) References Cited

U.S. PATENT DOCUMENTS 5,424,931 A * 6/1995 Wheeler ....................... 362/418
7,931,384 B2 * 4/2011 Bock et al. .................... 362/125

* cited by examiner

*Primary Examiner* — Stephen F Husar
*Assistant Examiner* — James Cranson, Jr.

(57) ABSTRACT

In an object verifier having a housing and an object holder, an object may be placed in the object holder for observation by an operator. The object is illuminated using a collimated beam of white light that is generated by a light generator. The collimated beam of white light is passed through a beam splitter with the two portions of the collimated beam of white light presented to the object at a 90 degree angle one from the other. The interior of the housing includes a reflective surface for maximal illumination of the object. The observer may view the illuminated object through a viewing window and/or through a magnification window. The magnification window provides for the viewing of the object in greater detail.

20 Claims, 13 Drawing Sheets

METHOD AND APPARATUS FOR OBJECT VIEWING, OBSERVATION, INSPECTION, IDENTIFICATION, AND VERIFICATION

FIELD OF THE INVENTION

The present invention relates to a method and apparatus for object viewing, observation, inspection, identification, and verification, and more specifically for the close examination of surfaces or small objects with low power magnification incorporating the use of controlled lighting.

BACKGROUND OF THE INVENTION

To determine the authenticity or identify distinguishing features of objects, and specifically of small objects, for example, gem quality stones, or small features on larger objects, for example, water marks on stamps, a number of methods have been used including the use of a jeweler's loupe, a magnifying glass, a microscope, or other similar apparatus, for purposes of magnifying the object or a portion of the object being viewed. The success of these methods depends on a number of factors, including the skill and training of the person viewing the object or portion of the object, on the availability of the proper accessory for providing the desired or necessary magnification, and on the availability of adequate and appropriate lighting conditions. In many instances only some but not all of these resources are available, providing a less than optimal environment for determining authenticity of or identifying objects. Even when all of these resources are available, their availability is usually limited and/or their quality is less than optimal.

Until recently, with the proper training, geological verification and identification was achievable using a jeweler's loupe. For example, a jeweler, through purely visual inspection using a jeweler's loupe, could distinguish between natural and synthetic diamonds. However, with the recent technological advances in the synthetic production of diamonds, it is no longer possible, or if possible it is very difficult, through purely visual inspection using a jeweler's loop to distinguish between natural diamonds and synthetic diamonds. In a documentary on Channel 13, originally broadcast on Feb. 1, 2000, a method for diamond verification was described that entailed the use of a laser tuned to a particular wavelength. The diamond under review is placed into a special holding apparatus and illuminated using this laser, which, in the case of synthetic diamonds, causes a fluorescence of the diamond, thereby revealing its synthetic origin. This method is of limited practical use since the cost of such lasers runs in the hundreds of thousands of dollars, the diamonds must be sent to the location where the laser is located, because the laser is large (and impractical to use) and difficult to transport, and it is a time consuming process to set up each diamond for verification by such a laser.

In the fields of numismatics and philately there are available apparatus for viewing and inspecting objects, such as, for example, coins or stamps, which provide a certain level of magnification. The usefulness of these apparatus are limited since they are bulky, must be worn on the face of the user, require external lighting and are costly. The alternative to these apparatus is the hand held magnifier glass, which provides for magnification of limited sections of the object and usually includes distortion and requires external lighting.

There is therefore, a need for a method, and apparatus that provides for the simple, cost effective, and efficient viewing, observation, identification and inspection of objects and object verification.

SUMMARY OF THE INVENTION

The present invention provides a method and apparatus for object viewing, observation, inspection, identification, and verification that overcomes the limitations of the prior art. More specifically, the present invention provides a method and apparatus for object viewing, observation, inspection, identification, and verification where all of the necessary functions are provided in a single piece of equipment or multiple pieces of equipment operating together, which is of compact size, low cost and easy to use.

The present invention also provides a method and apparatus for controlled illumination, which may include, for example, control of the wavelength and/or color temperature of a light source. The present invention also provides a method and apparatus for positioning an object, which may include, for example, providing a viewing area that permits the controlled illumination to be the dominant source of light for the object or surface of the object even with relatively high ambient light conditions, and which may also include a positioner for placement and securing of objects, for example, small gem stones, coins, postage stamps, etc. The present invention also provides a viewing window, which may include, for example, the incorporation of selective magnification and which protects the viewer from UV radiation that may be generated by the illumination wavelengths selected.

The present invention can be used where known apparatus provide sub-optimal results, require a controlled environment for use (which is often not available), or require specialized training. For example, features in gems, such as, for example, flaws, may be examined and identified using a jeweler's loupe, but certain features may not be discernable by a person not specifically trained or experienced in the use of such a device. The present invention allows a novice to examine gems and identify specific features, including, for example, flaws, without the need for any specialized training or experience. The present invention also allows for the inspection of other objects and their features in detail under controlled conditions. For example, the present invention can be used for inspecting paintings, coins, artifacts, forensics, crime scenes, coatings, etc.

The present invention can also be used, for example, for distinguishing between natural gem quality stones, including diamonds and a number of types of synthetic gem quality stones, including diamonds, and for dating and authenticating works of art, such as, for example, oil paintings. The object verifier according to the present invention provides the necessary illumination at the proper frequency for inducing the fluorescence of a synthetic gemstone and various pigmentations.

The object verifier according to the present invention may also provide for the proper positioning of the gemstone or other object, and/or for magnification of the gemstone or other object. The object verifier may also provide for select levels of magnification corresponding to one or more positions of, or locations on, the gemstone or other object.

The present invention provides a method and apparatus for object viewing, observation, inspection, identification, and verification for geological materials, including, for example, minerals and crystals, vegetation, including, for example, plant reproductive systems and leaf structures, and animals, including, for example, insects, arachnids and reptiles. The present invention also provides a method and apparatus for object viewing, observation, inspection, identification, and verification for a multitude of small man-made objects, including, for example, postage stamps, anthropologically significant handicrafts, such as, for example, arrow heads, beads, and decorative items, antique, art, or collectable items, a wide range of manufactured objects where visual inspection is required for quality control, and a wide variety of locations where features and details require examination.

The present invention provides for each individual, and all possible combinations, of the following features: illumination control—which provides control over the wavelength and/or color temperature of the light source; an illumination/viewing area—which permits the illumination of an object to be accomplished using the dominant lighting for the surface/object even with relatively high ambient light conditions; and a viewing window—which incorporates selective magnification for various portions of the surface/object and protects the viewer from exposure to UV radiation that may result from the illumination wavelength used. In one possible embodiment, the illumination/viewing area may include an object holder so that small objects, such as gem quality stones, may be secured and/or advantageously positioned, for example, for detailed examination and evaluation. The illumination/viewing area may also or alternatively include a mirrored or transparent surface on which the object is positioned, for example, for detailed examination or viewing.

The illumination control includes a high quality 'white' light source, such as, for example, a tungsten-halogen lamp (known for its efficient and uniform light quality over the life of the lamp) with a 'universal' power source (100-240 vac input). Additionally, beam-forming optics will provide a beam profile and focal length suitable for the subsequent manipulation by the illumination control components.

The beam forming optics may be designed, for example, such that the beam profile will become relatively collimated and then divide into two beams which diverge at about a right angle—the angle being in the plane parallel to the subsequent viewing window and roughly parallel to the surface that may be the subject of examination as the beam(s) enter the illumination/viewing area.

After the initial beam profile has been established, and prior to the beam division just described, a wavelength or color temperature selection element may be provided that functions to 'filter' the light such that the emerging light quality is of a desired characteristic. This characteristic can include: a) the apparent color of the light—that can be specified by a relatively wide range of wavelengths; b) the exclusion of a particular narrow range of wavelengths; c) the inclusion of a narrow range of wavelengths; d) more than one narrow range of wavelengths; e) light of a particular 'color temperature'—that is the full range of visible wavelengths where the distribution of wavelengths is shifted to a particular characteristic of light, e.g. daylight, or 'tungsten' lighting; and f) other light qualities.

The above 'filtration' can be best achieved through the use of holographic optics because of their ability to provide the complex optical processing in a very thin optical element. Further, the use of a holographic grating can permit the user to adjust the apparent color of the light by means of a knob that changes the grating's angle within the light beam. However, any type of optics, software or data manipulation may be used to perform such 'filtration.'

A second illumination source may be included to provide UV light in a similar configuration to that for white light on UV compatible instruments and objects. The UV illumination optics will, of necessity, be different than those used for visible light. These optics and the holographic optics will be suitable for the 'near-UV' wavelengths, and this illumination source will only share a common exit aperture with the white light source as the light enters the illumination/viewing area.

The UV illumination is preferred for the examination and verification of diamonds, other gemstones, and minerals as well as for the examination of pigments in paintings. Should the unit be targeted for the inspection of commercial quantities of diamonds (for instance) a special high intensity hard UV source could be coupled to the unit, and the viewer's eyes and skin would continue to be protected by the viewing window's UV blocking properties. This would permit suspect synthetic stones to be quickly segregated from natural stones in large groups.

The goal of the illumination/viewing area is to (a) provide relatively uniform illumination to all surfaces and/or objects positioned within the illumination/viewing area, and to (b) position the viewing window at the optimum location for observation, inspection and examination of the surface and/or object by the viewer. The illumination/viewing area may also include object positioning hardware, for example, an object mount (such as used for positioning gemstones), or a surface for positioning an object, such as, for example, a mirrored or transparent surface.

The illumination/viewing area may be designed such that a first portion of the illumination/viewing area will include an aperture for introduction of the beam(s) by the illumination control, as described above. As described above, the illumination may comprise, for example, two roughly collimated beams of light offset by approximately 90 degrees from one another emerging from this aperture. As these beams enter the illumination/viewing area, one of the beams will encounter the 'upper' interior wall of the illumination/viewing area while the other will encounter the 'lower' interior wall of the illumination/viewing area.

To achieve the highest uniformity of illumination toward the surface and/or the object, the interior surface(s) of the illumination/viewing area will be comprised of a 'white' (very broad band) diffusely reflective surface(s), formulated to also be diffusely reflective and not fluorescent for UV wavelengths. Alternatively, the interior surface(s) may be less reflective or not as diffusely reflective as a 'white' surface(s). These surface(s) will include a surface contour that directs a portion of the reflected light toward the surface and/or object to be illuminated. In addition, a portion of the interior surface near the illumination aperture will be contoured to reflect a portion, and preferably, a significant portion, of the incident light back toward the wall surface adjacent to the illumination aperture.

A significant portion of the reflected light from the 'upper' and 'lower' interior walls of the illumination/viewing area will exhibit surface reflection, and be directed toward the 'end' wall of the illumination/viewing area, opposite the illumination aperture. This wall surface, as well as the wall surface adjacent to the illumination aperture should have the same or similar reflective characteristic as previously described.

The path of the illumination beams will circle the central region of the illumination/viewing area, and the diffusely reflected light will also be reflected from the 'inside' of the viewing window to provide additional surface or object illumination. Should a particular application require greater illumination from the location of the viewing window, a reflective or refractive coating, such as, for example, a broadband dielectric coating, may be used to enhance the reflective illumination provided by or from this surface.

The illumination/viewing area may be designed such that the positioning surface is located at the lower portion of the illumination/viewing area and the viewing window is located at the upper portion of the illumination/viewing area. The positioning surface, if comprised of transparent material, may be offset from the bottom of the illumination/viewing area such that any light directed toward the object may be reflected from the bottom surface of the illumination/viewing area for further illumination of the object. Where the positioning surface is comprised of reflective material, there may be a designed-in offset between the reflective portion and an adjacent transparent portion such that the light directed toward the object may be reflected back toward the bottom portion of the object for enhanced illumination. The viewing window may have the same properties as described above, and/or may include a curvature, such as, for example, to provide a substantially uniform distance from each position of the viewing window to the object, to minimize distortion of the object being viewed.

The viewing window may be used to augment the illumination of a surface and/or object, and may include magnification zones for magnifying those portions of the surface and/or object detail viewed through the magnification zone portions of the viewing window. The magnification zones within the viewing window may be provided using 'off-axis' magnification, thereby requiring a complex or other type of lens system.

For example, holographic elements may be used to provide the magnification zones within the viewing window. Holographic elements are appropriate because they do not have the bulk or fabrication costs associated with magnifying lenses, and in particular the type of magnifying lenses necessary for use in 'off-axis' magnification, but are able to provide the complex functionality necessary for providing the desired magnification. Alternatively, lenses or other optical elements may be used.

As an example of a configuration for the viewing window, there would be provided a clear (non-magnified) view of the surface and/or object at the central region of the viewing window, and a number of independent magnifying zones to enlarge portions of the surface and/or object, for example, three zones, with one located at each of the upper, lower-left and lower-right zones of the viewing window. These magnifying zones may range from relatively low power (e.g., 1.8 to 2.5×) to a somewhat higher power (e.g., 5.5 to 8.2×), and even to a higher power, and could be useful for a wide range of uses, for example, from biological and geological specimen examination to textile and printing inspection.

Viewing windows may be provided for a variety of specialized purposes, to include greater magnification, magnification zones in special locations and at powers up to 8× or even greater. For UV examination of fluorescence and phosphorescence, for example, for gemstones or paintings, the viewing window would provide the viewer with protection from the harmful effects of UV radiation on the eyes and skin, or as discussed below, can provide an image of the object on a display or other device at a remote location.

The present invention also provides for an object positioner, to allow for the holding and positioning of objects, for example, individual gems as well as the positioning of small objects for examination within the object verifier. The object positioner is useful, for example, for examination and appraisal of jewelry and gemstones. It permits a quick and simple examination and allows for extended use, i.e., for a number of hours, without the eyestrain normally attendant to certain viewing activities, such as, for example, gem categorization, sizing, and separation, numismatic portfolio appraisal, etc. The object positioner is easily adapted to be used in the illumination/viewing area. For example, it can be mounted to the 'back' opening or bottom of the illumination/viewing area, or at some other location.

The object positioner may be rotatable such that the object may be positioned for viewing from any angle. The object positioner may be fully adjustable and/or rotatable in all directions and all axes. The adjustment/rotation may be accomplished and/or controlled manually or through one or more motors and may provide for rotation in one, two or three dimensions, such that the position of the object may be adjustable about all three axes and in all directions.

The present invention also provides for a fiber optic spot illuminator, to allow for the independent illumination of portions of the surface and/or object being viewed. The fiber optic spot illuminator includes an illumination source that can be easily introduced into the illumination/viewing area, and positioned to provide a directed beam of light (like a spotlight) to a particular location or at a very precise angle to the surface and/or object. The illumination source may be, for example, a generic 'white' light fiber optic illuminator that would have a relatively low cost. Alternatively, the illumination source may incorporate all of the illumination color and wavelength control of the verifier illumination described above. This would be more costly, and would provide the same or different illumination characteristics to the surface and/or object than that provided by the verifier unit itself.

The present invention also provides for a manipulation adaptation, which would allow for the manipulation of objects within the illumination/viewing area. The manipulation adaptation would incorporate one or more openings in one or more walls for the introduction of tools and/or instruments for the manipulation of an object within the illumination/viewing area. This would permit, for example, the dissection of a biological specimen within the controlled illumination of the verifier and under low to high power magnification. This activity could be easily captured on video or some other recording medium, or relayed to video monitors or some other display device for real-time demonstration or instruction.

The present invention also provides for the use of the device in many different configurations, including, for example, as a partial housing (without a rear portion), as a flat or curved lens having no housing, or as any other portion of a housing, so that examination of a portion of the surface of relatively large objects or locations might be accomplished. These large objects may include, for example, paintings, pottery, furniture, textiles, printed or hand written documents, and locations may include, for example, archaeological sites, crime scenes, coated surfaces, etc.

The present invention also provides for a camera mount, which would allow for the mounting of a camera or other image capture device to the illumination/viewing area. The camera mount may include any number of legs to support a camera or other recording device, and would allow for the recording of the surface or object under examination, for example, by conventional photography, digital photography, video, etc. A more advanced camera mount would include adjustments for the leg lengths so that the camera or recording device may be positioned to view the object through any window or magnifying zone desired.

The present invention may also include, as part of the housing or as a separate element, an image capture device or system, such as, for example, a CCD or other digitizing image capture device, for purposes of capturing images of the object being viewed. The image capture device may be positioned within the interior of the housing or at an aperture of the housing. The data from the image capture device may be sent to a data storage device, such as, for example, CD-ROM, DVD, RAM, ROM, hard drive, memory card, volatile or non-volatile memory, optical data storage tape drive or any other data storage medium or device, or to a computer or display device, such as, for example, a LCD monitor, CRT screen, or any other display medium or device, or to a printer or some other image presentation device, for purposes of viewing an object located in the illumination/viewing area, archiving information about the object or for other image capture or storage purposes. For example, the image data captured by the digitizing image capture device may be used for purposes of generating a hologram of the object.

The present invention may also or alternatively include, as part of the housing or as a separate feature, a spectral analyzer system, using, for example, a fiber optic probe or lensing system, to capture light from the object and perform a spectral analysis on the constituents of the light from the sample. The fiber optic probe or lensing system may direct a portion of the light reflected from the object to a spectral analyzer integral with or coupled to the housing or to a separate spectral analyzer that may be located adjacent to the housing or at a remote location. The spectral analyzer may be used to provide additional information about the object, such as, for example, chemical composition, molecular structure, or age of the object, beyond the information that can be determined by a mere visual inspection, irrespective of the magnification capability of the system.

The present invention may also be used as a mini-studio for capturing image data of an object for generation or creation of a hologram, for example, using V-3D as described in U.S. Pat. No. 5,748,347, at a location within the housing or at a remote location. Such image data capture may be accomplished in real-time or at a later point in time from archival data records.

DETAILED DESCRIPTION

Figure 1:
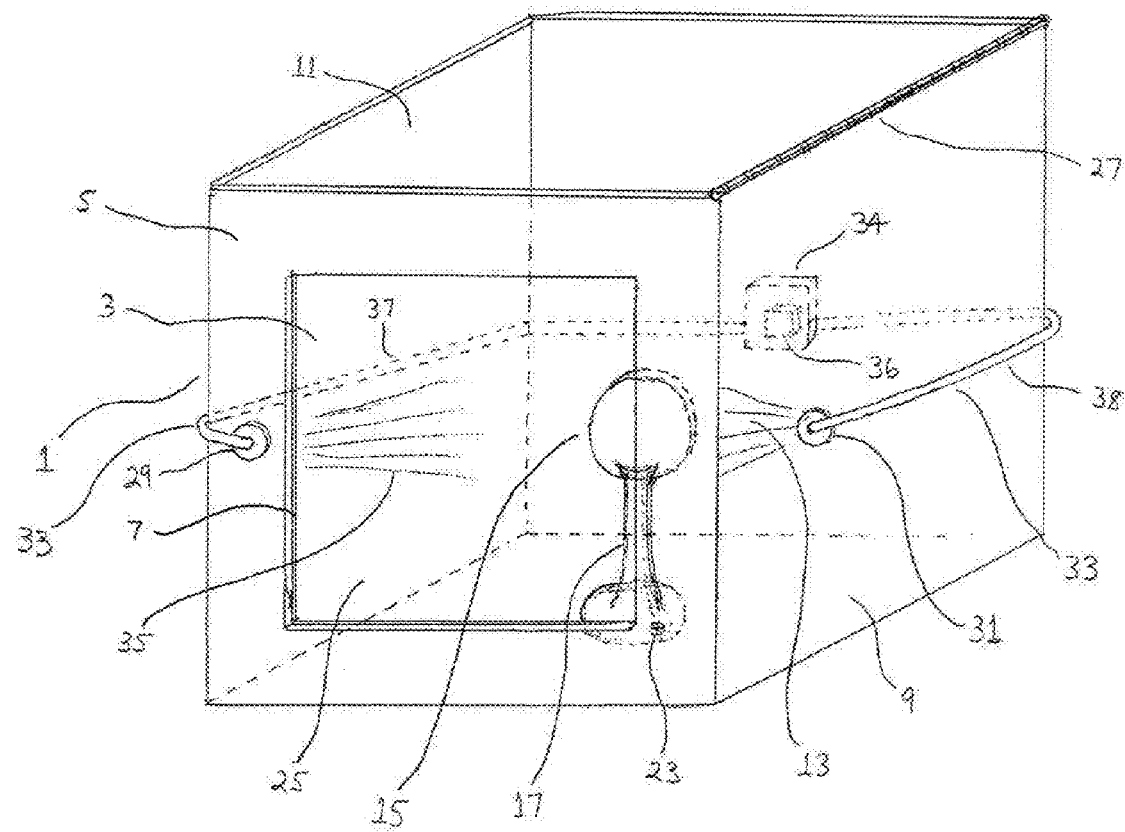
FIG. 1 shows an object verifier according to an exemplary embodiment of the present invention

An exemplified embodiment of an object verifier according the present invention is shown in FIG. 1. This embodiment of a verifier includes a housing 1, in the shape of a cube. Alternatively, the housing may be of any three dimensional shape, including, for example, pyramid, sphere, ovoid, cylinder, octahedron, tetrahedron, polyhedron, spherical, etc., or a portion thereof, for example, a hemisphere. The housing 1 includes a viewing window 3 formed integrally with a first side-wall 5 of the housing 1, or fitted within a frame 7 formed in the first side-wall 5 of the housing 1. The exterior surface of the housing 9, excluding the viewing window 3 may be coated with a protective or decorative material, such as paint, rubber, lacquer, laminate, decals, etc. The interior surfaces of the housing 11 forms an area 13 within which an object 15 is located. The interior surface 11 of the housing, including or excluding the viewing window 3, may be coated with a reflective coating, preferably a low-loss type of coating. Alternatively, the interior surface 11 may be uncoated or have any type of coating. The area 13 includes an object holder 17 into or onto which the object 15 is placed. The object holder 17 is mounted onto the interior bottom surface 19 or a side surface 21 of the housing, using an anchor 23, such as, for example, a screw or rivet, by temporary or permanent bonding, such as, for example, adhesive or welding, using Velcro, or some other anchoring device. Alternatively, the object holder 17 may simple be placed within the housing 1 without being attached thereto. The interior surface of the viewing window 25 may be left uncoated or may be coated with a dielectric material, such as, for example, $ZrO_2$ or $TiO_2$, which will enhance the illumination of the object 15. The housing 1 includes two illumination windows 29, 31 offset one from the other, with the first illumination window 29 located next to the viewing window 3, and the second illumination window 31 located on a side of the housing 1 adjacent to the viewing window 3. Alternatively, there may be one or any number of illumination windows at various locations as desired. The interior surfaces of the housing 11 are contoured such that the light reflecting off of such surfaces is directed primarily toward the opposite surfaces, i.e., the surfaces where the illumination windows 29, 31 are located. Alternatively, the interior surfaces may be flat or have any shape or contour. A hinged or removable upper portion 27 is provided for the housing 1 to allow for access to the interior, as well as insertion, removal, and manipulation of the object 15. Alternatively, the top of the housing 1 may be open, or in place of a removable or movable upper portion, there may be a wall portion or bottom portion of the housing that may be open, removable or movable. The housing may not include an object holder, but instead the object may be placed on the bottom surface of the housing 1.

Coupled to the illumination windows 29 and 31, via a fiber optic cable 33 (or other light transmitting wave-guide), is a light generator 34. The light generator 34 provides a collimated beam of white light 35 that is used to illuminate the object 15. The collimated beam of white light 35 passes through a beam splitter 36 prior to entering the fiber optic cable 33. The fiber optic cable provides two paths for the collimated beam of white light 35, the first path 37 leading to illumination window 29 and the second path 38 leading to illumination window 31. Alternatively, the light generator 33 may provide a beam of light of a select wavelength or group of wavelengths, such as, for example, UV band, or ER band. Aside from directly illuminating the object 15, the collimated beam of white light 35 is also reflected from the opposing interior surface of the housing 39 to the other interior surfaces 11 of the housing 1. This reflection of the collimated beam of white light 35 provides for enhanced illumination of the object 15. The light generator 33 may be powered by a DC power source, such as, for example, battery, or by an AC power source. Alternatively, there may be no splitting of the collimated beam of white light 35, and only a single illumination window, or there may be splitting of the collimated beam of white light into any number of portions with a corresponding number of illumination windows. The beams of light may be transmitted to the interior of the housing via some other means of transmission. Alternatively, the light generator may be a semiconductor diode laser or some other light source directly coupled to the housing with no need for a fiber optic cable or other transmitter. The light used for illumination may also be non-collimated or of any shape or structure.

Figure 2:
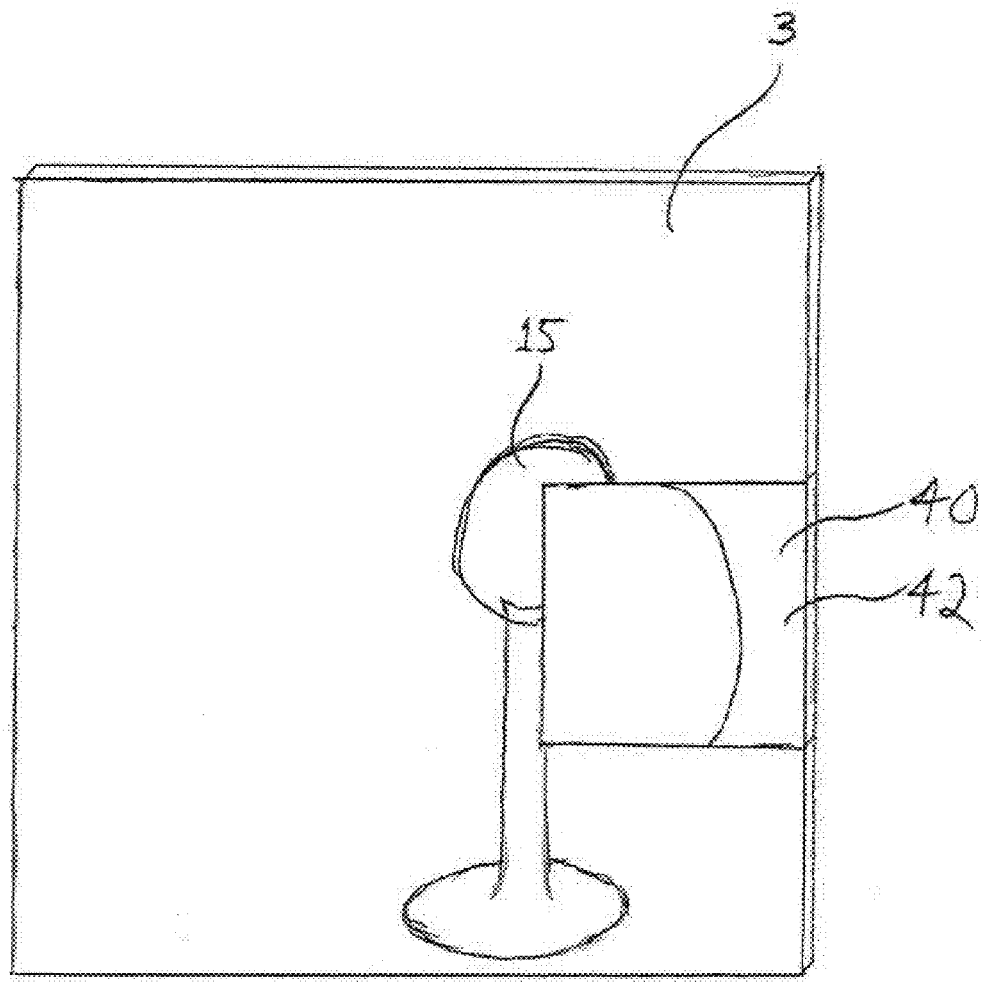
FIG. 2 shows an enlarged view of the magnification window of the object verifier of FIG. 1.

As shown in FIG. 2, in an embodiment according to the present invention there is a magnification window 40 positioned within the viewing window 3. The magnification window 40 includes an holographic element 42 for enhancing the viewer's access to information contained in or on the object 15. Alternatively, the viewing window 3 and magnification window 40 are formed from a single holographic element, with the magnification window 40 located in a particular portion of the viewing window 3. There may be any number of magnification windows as separate elements or as part of the viewing window 3 or combined together into any number of separate windows.

Figure 3:
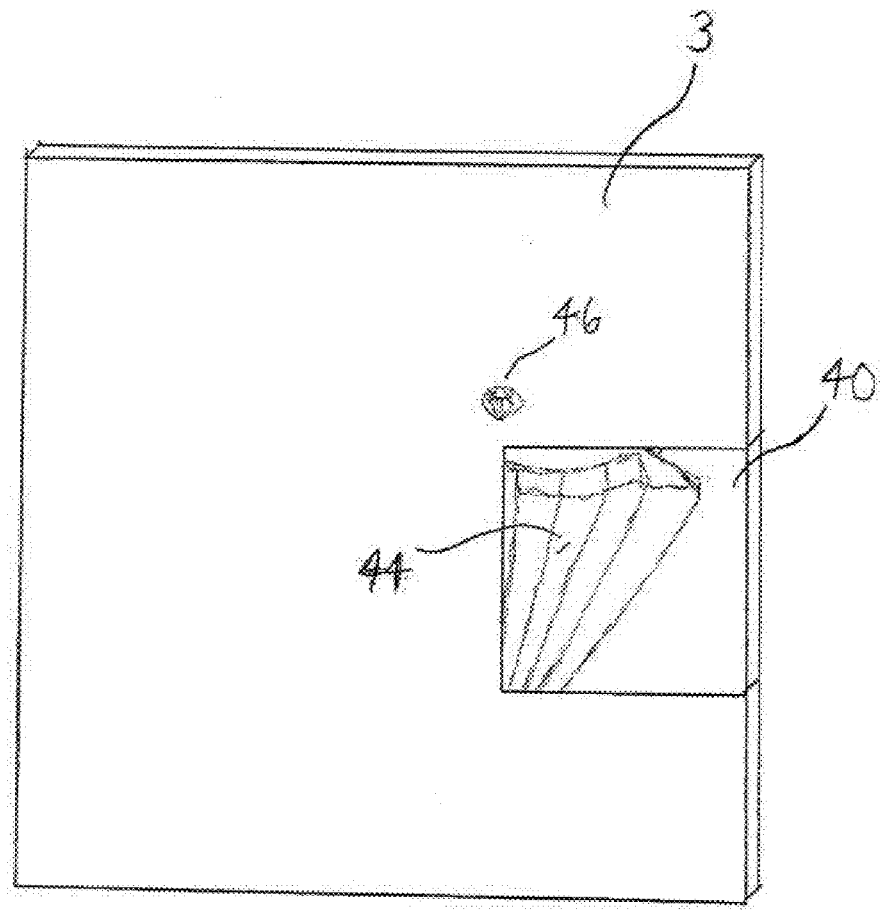
FIG. 3 shows a diamond as viewed through the magnification window of the object verifier of FIG. 2.

As shown in FIG. 3, a flaw 44 in an object, in this case a diamond 46, being viewed through the magnification window 40, which would not be visible to the naked eye, is clearly visible even to an untrained viewer. The magnification window 40 increases the size and enhances the clarity of the viewable image of the diamond 46 through magnification and controlled lighting of the diamond 46.

Figure 4:
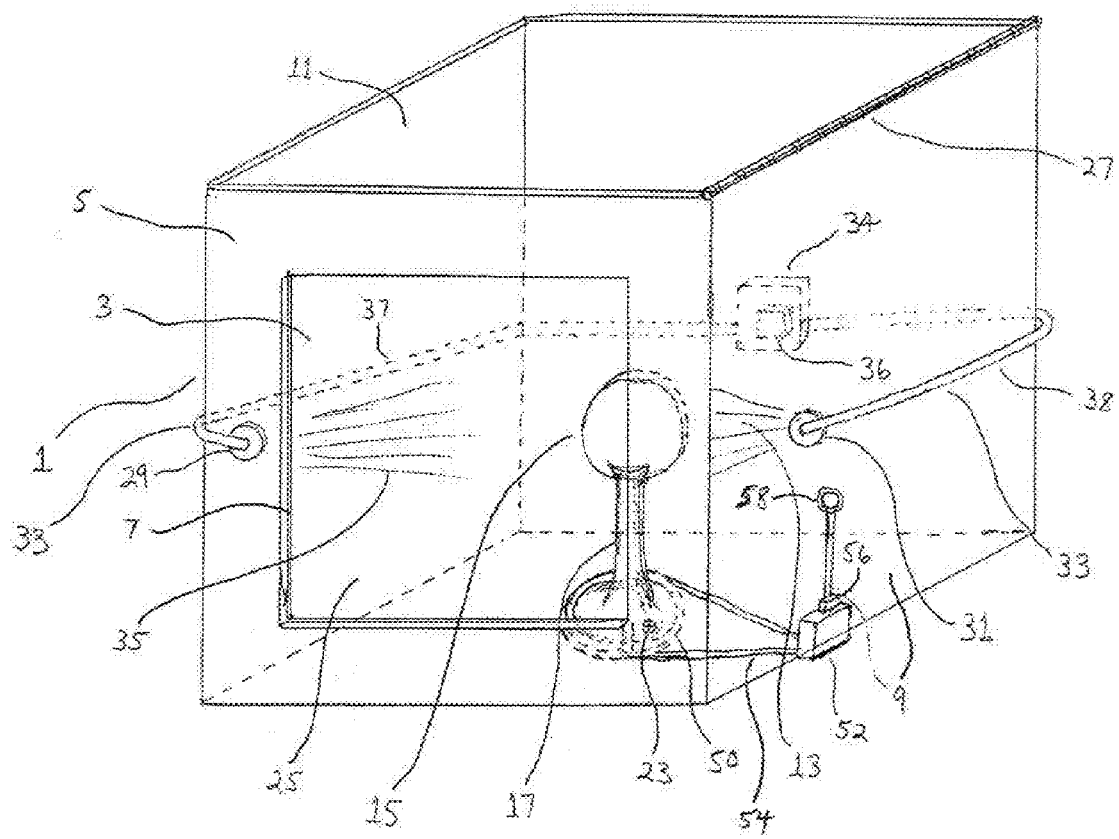
FIG. 4 shows an object verifier having a rotatable object holder according to an embodiment of the present invention.

In FIG. 4, there is shown an embodiment of the present invention where the object 15 may be rotated within the housing 1. In this embodiment, the object holder 17 is mounted onto a disc 50. The disc 50 is coupled to a motor 52 via a belt 54, that provides for the rotation of the disc 50, and in turn, the rotation of the object holder 17 and the object 15. The movement of the motor 52 is controlled by a control circuit 56 and is operated by the viewer, using a switch 58.

Optionally, there may be a speed control that allows the viewer to control the speed of rotation of the object 15.

Figure 5:
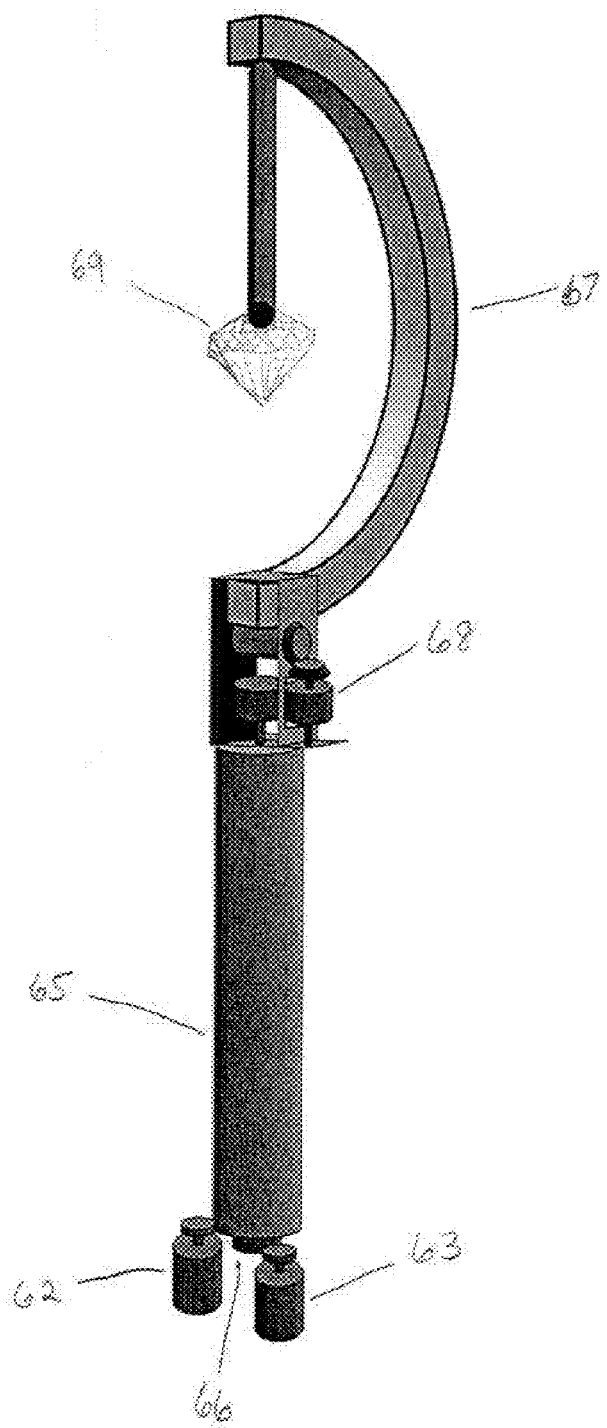
FIG. 5 shows an object verifier having a rotatable object holder and gearing for rotation of the object about multiple planes, according to an embodiment of the present invention.

As shown in FIG. 5, there may optionally be first gear 62 coupled to the motor 52, and second gear 63, coupled to a second motor 64. The first gear 62 is coupled to a first shaft 65 that is cylindrical with the central portion being hollow, and the second gear 63 is coupled to a second shaft 66 that runs through the center of the first shaft 65. The first shaft 65 is coupled to an object holder 67, and the second shaft 66 is connected to a third gear 68. The first gear 62 and the first shaft 65 provide for the rotation of the object holder 17 and thereby an object 69 about a first axis. The third gear 68 is coupled to the object holder 17 to provide for the rotation of the object holder 17 and thereby the object 69 about a second axis. This configuration provides for the rotation of the object 69 in more than one plane. Alternatively, the object 69 may be placed directly on the disc 50 or on any other object that is coupled to the motor or manual device for rotation of the object 69.

Figure 6:
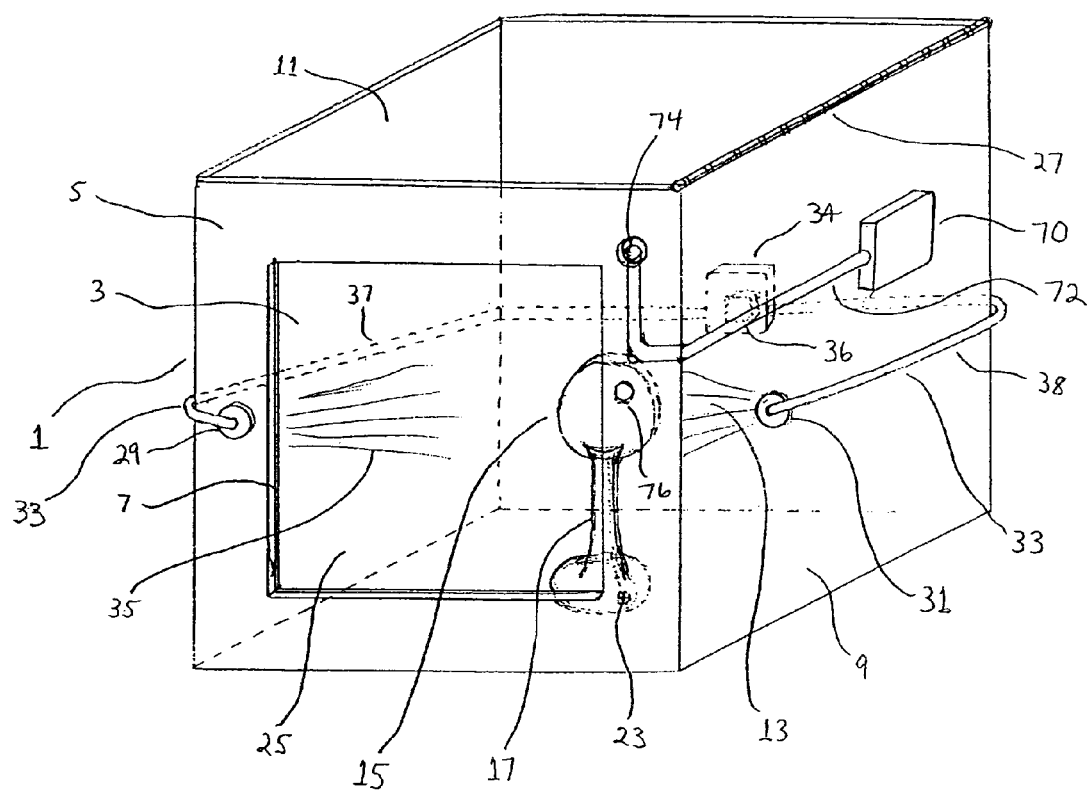
FIG. 6 shows an object verifier having point illumination according to an embodiment of the present invention.

Turning to FIG. 6, there is shown an embodiment of the present invention that includes point illumination of portions of the object being viewed. A spot illumination light source 70, is coupled to the housing a fiber optic cable 72 or other type of light waveguide. A spot illuminator 74 is positioned at a location in the housing that will allow for the point source illumination of a predetermined location in space that corresponds to a point 76 on the object 15 when the object 15 is positioned with reference to the viewing window 3. The point illumination may be provided by any other illumination device, including, for example, a laser diode, laser or direct light source. The point illumination may also be provided using one or more mirrors to focus the light at a particular location. This point illumination may be adjusted to any size or location in the housing 1 through control of the spot illumination light source 70.

Figure 7:
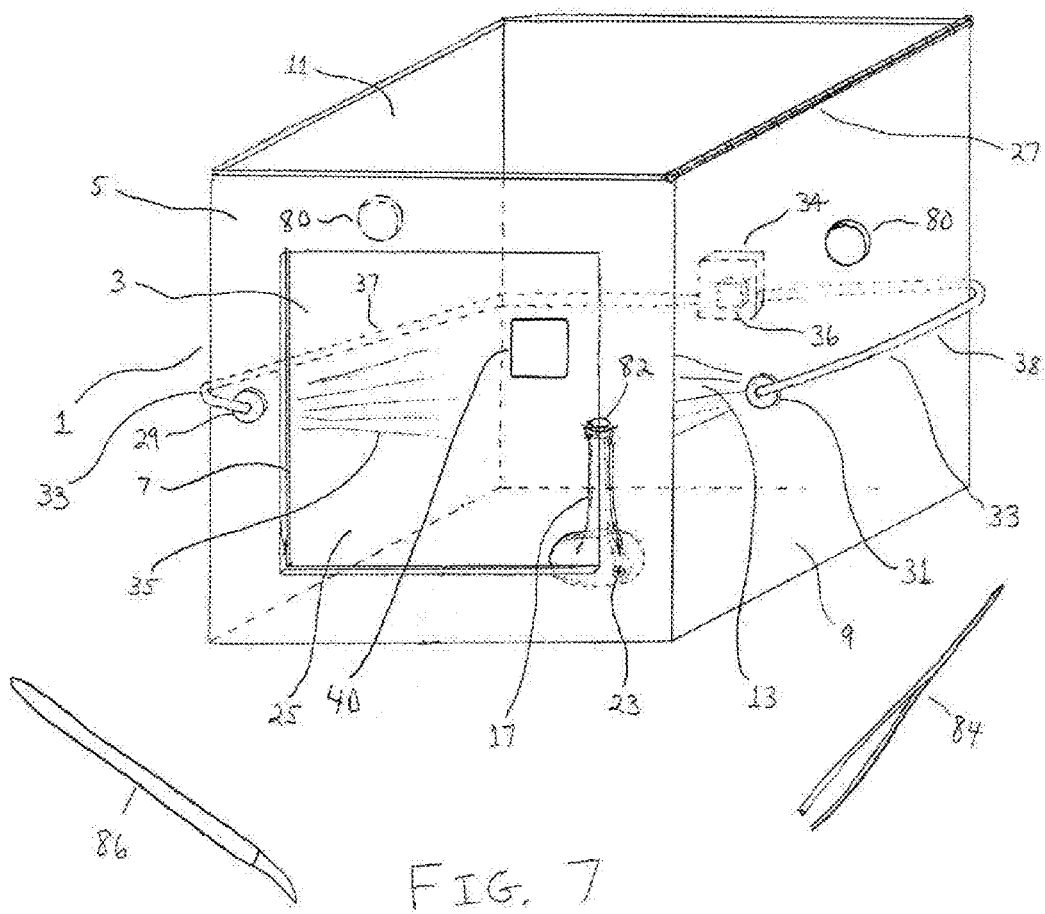
FIG. 7 shows an object verifier having apertures for manipulation of the object according to an embodiment of the present invention.

FIG. 7 shows an embodiment of the present invention that includes apertures in the housing that provide for object manipulation. The housing 1 includes two apertures 80 through which manipulation tools may be inserted into the housing 3. For example, where the object is a biological specimen, such as a deer tick 82, the manipulation tools could be a tweezer 84 and a scalpel 86 for dissection of the deer tick 82. The magnification window 40 would provide for an enlarged view of the deer tick 82 and the scalpel 86 to assist the operator in the dissection of the deer tick 82, and to aid the viewer in identifying the various features of the deer tick 82 as it is being dissected. The use of the spot illumination light source 70 from FIG. 6 could also aid in the viewing of the dissected deer tick 82. Alternatively, there may be sealed openings through which gloves are inserted or attached for isolated manipulation of the object, when the issue of contamination may be involved.

Figure 8:
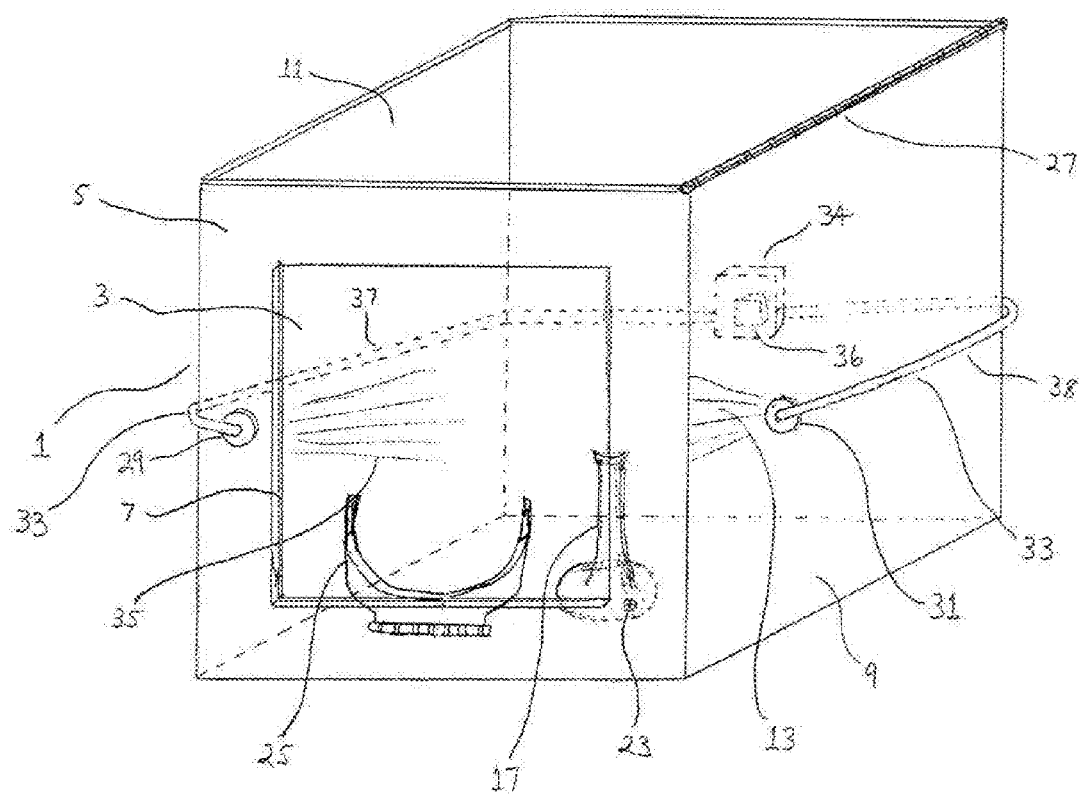
FIG. 8 shows an object verifier that provides for the mounting of an image capture device according to an embodiment of the present invention.
Figure 9:
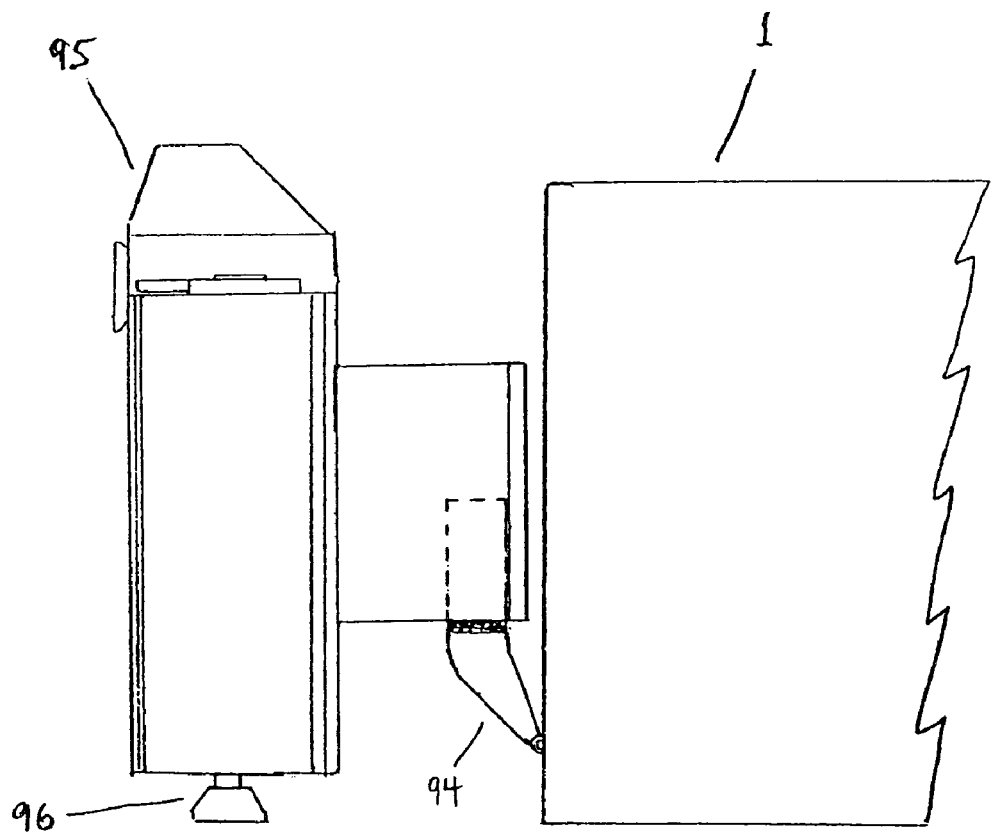
FIG. 9 shows the object verifier of FIG. 8 with a camera mounted thereto.

As shown in FIG. 8, there is shown an embodiment of the present invention that provides for the mounting of an image capture device to the housing. There is provided at the viewing window 3 or at the magnification window 40 a camera mount 94 that would allow for the mounting of a camera 95 or other image capture device to the housing 1. FIG. 9 shows the camera 95 coupled to the camera mount 94. The camera 95 includes at least one support leg 96 such that the weight of the camera will not cause the housing 1 to become unstable. The activity of the operator, such as, for example, the dissection of the deer tick 82 described above, may be easily captured on film or video or some other recording medium for storage, or later viewing or playback, or relayed to a video monitor or some other display device for real-time demonstration or instruction. Alternatively, the image capture device may have access to a view of the object through a dedicated aperture or mounting location on or in the housing 1.

Figure 10:
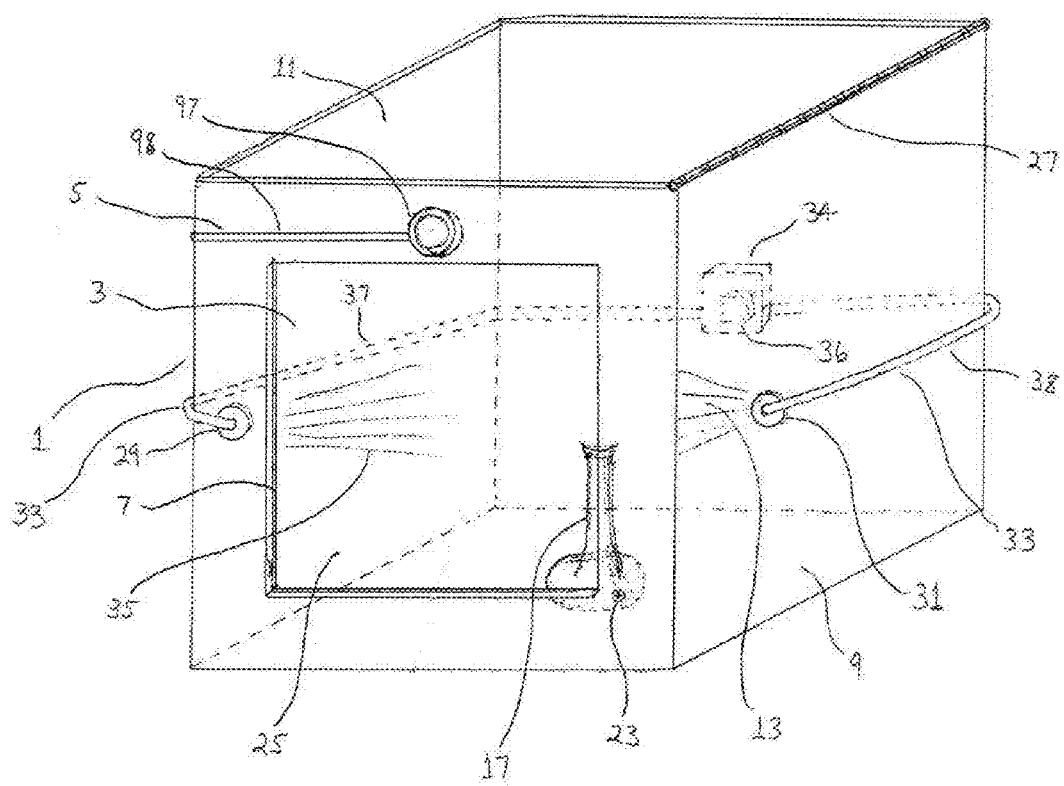
FIG. 10 shows the object verifier of FIG. 1 including a digital image capture device.

FIG. 10 shows the embodiment of the invention as described with respect to FIG. 1, further including a digital image capture device 97. The digital image capture device 97 may include, for example, a CCD or digital detector, and may be located within the housing 1. The digital image capture device 97 may be used, for example, to provide a digitized view of the object 15, for archiving of the digital data, for viewing the object and/or for reproducing a holographic or three-dimensional image of the object 15. The digital image capture device may also transfer the image of the object 15 to a display device via cable 98 for viewing the object 15 in real time and/or in enhanced form. Power for the digital image capture device 97 may be obtained from a battery or other power supply.

Figure 11:
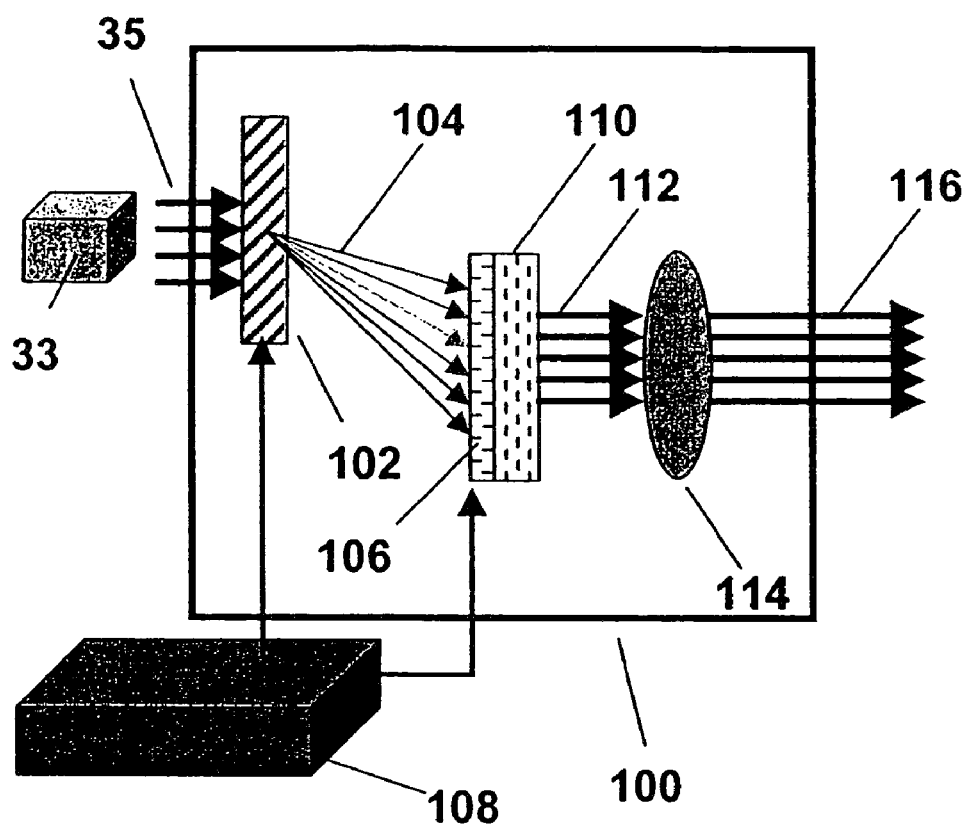
FIG. 11 shows a wavelength selection element according to an embodiment of the present invention.

FIG. 11 shows a wavelength selection element 100 according to an embodiment of the present invention. The wavelength selection element 100 that is coupled to the light generator 33 acts as a filter for the collimated beam of white light 35. The wavelength selection element 100 includes a holographic optical element 102 through which the collimated beam of white light 35 passes. The holographic optical element 102 processes the collimated beam of white light 35 and directs the processed beam of light 104 onto a holographic grating 106. The holographic grating 106 includes a controller 108 for adjusting the angle or position of the holographic grating 106 with respect to the processed beam of light 104. In place of the controller 108, a motor, mechanical adjustment, and/or switch may be used to automatically adjust the angle or position of the holographic grating 106. The processed beam of light 104 is reflected off of, by and/or through the holographic grating 106 and then through one or more apertures in filter 110 to provide a filtered light beam 112. The angle or position of the holographic grating 106 in conjunction with the various apertures of filter 110 determines the characteristics of the filtered light beam 112 that is reflected off of, by and/or through the holographic grating 106. After passing through one or more apertures of filter 110, the filtered light beam 112 passes through a second holographic optical element 114 that serves to collimate the filtered light beam 112 to provide a tuned light beam 116. The wavelength selection element 100 may be used to adjust the wavelength of the light provided to the verifier. By adjusting the holographic grating 106 and the apertures of filter 110, the wavelength selection element 100 may be used to exclude particular wavelengths of light, include particular wavelengths of light, provide a particular color temperature for the light, select or exclude a single wavelength, adjust the amplitude of the light, or provide for other light modification techniques. Alternatively, the adjustment of the light may be accomplished using optics, or software or data manipulation in place of the grating and aperture structure described above. As an alternative to the mechanical apertures of filter 110, a spatial light modulator (SLM) may be included to intercept the light from the holographic grating 106. The SLM may be controlled by software to dynamically include and/or exclude one or more selected wavelengths from the holographic grating 106. The SLM can provide more subtle control of the filtered light beam 112 by allowing the construction of a filtered light beam having very specific characteristics. The SLM operates under software control, similar to the way a LCD can be used to reconstruct an image (as in a computer display). The SLM operates on the phase and amplitude of the light with which it interacts, and can be controlled to provide a grating structure that can be instantly changed to a different grating structure under software control. When a broadband light illuminates the SLM, the SLM will interact with the selected grating structure to produce a particular spectral dispersion (a dispersed spectrum as from a prism or simple grating) such that a desired narrow portion of the spectrum falls on an exit aperture and passes on as filtered light beam 112. It is also possible, through the software control, to change the SLM grating structure so as to provide a number of different narrow portions of the spectral dispersion to the exit aperture in rapid succession. By controlling the time duration of each of the portions thus selected, it is possible to present a precisely controlled spectral profile as the filtered light beam 112.

Figure 12:
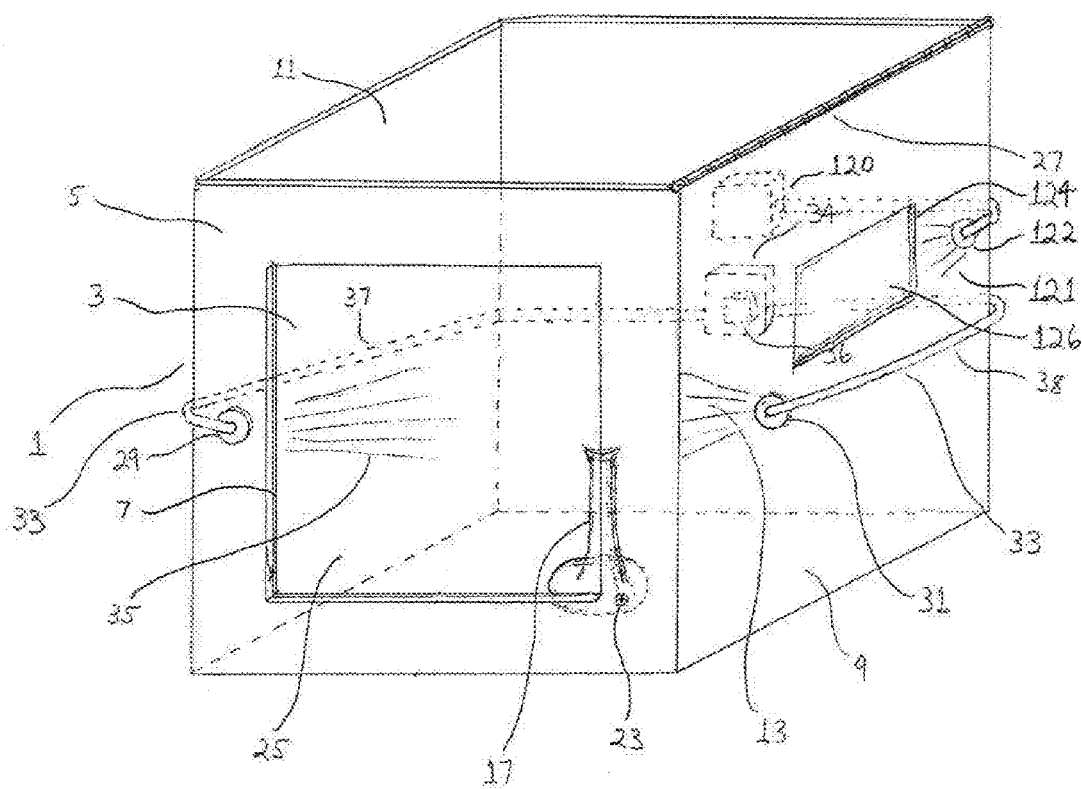
FIG. 12 shows an object verifier having a white light generator and a UV light generator, according to an embodiment of the present invention.

As shown in FIG. 12, a second light generator 120 may be included with the object verifier to provide UV light 121 to the housing through an UV illumination window 122. This may be used for purposes of use with UV compatible instruments and objects requiring UV illumination. A second viewing window 124 is provided that includes a UV holographic element 126. The UV holographic element 126 is suitable for the 'near-UV' wavelengths, and the UV light 121 provided by the second light generator 120 may either share common apertures with the illumination windows 29, 31 for purposes of providing UV light 121 to the interior of the housing 1, or it may be transmitted through separate apertures. If the UV light 121 shares common apertures with the collimated beam of white light 35, coupled to the light generator 33 and the second light generator 120 may be a combiner for combining the UV light 121 and the collimated beam of white light 35. The viewing window 3 would include a UV filter 128 to protect the viewer from the UV light reflected back from the interior surfaces of the housing 11 and the object 15. The second light generator may be a laser, laser diode, or some other type of light source.

Figure 13:
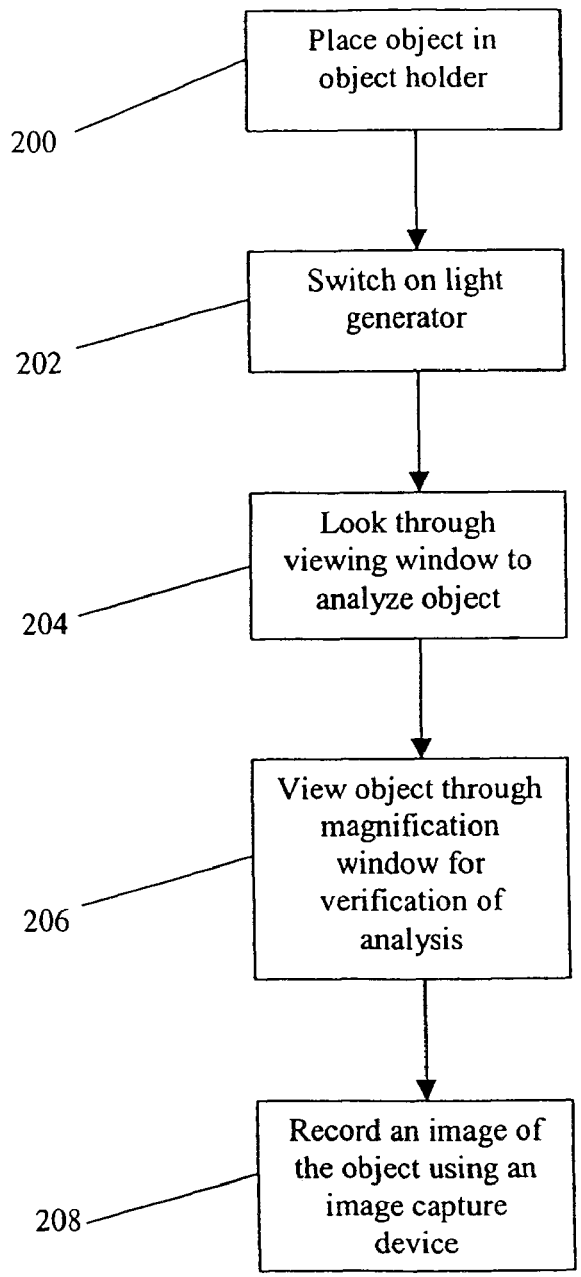
FIG. 13 shows a method of object verification according to an embodiment of the present invention using the object verifier of FIG. 1.

FIG. 13 shows a method of performing an object verification using the object viewer of FIG. 2. In step 200, the object 15 to be analyzed is placed in the object holder 17. The light generator 33 is switched on in step 202, providing a collimated beam of white light 35 for illumination of the object 15. In step 204, the operator looks through the viewing window 3 for purposes of analyzing the object 15. In step 206 the operator may view the object through the magnification window 40 to verify the analysis of the object or to observe the object 15 in further detail for purposes of analyzing the object 15. The operator may use an image capture device in step 208 to record an image of the object 15 for memorialization or archival purposes.

What is claimed is:

1. An object viewer providing for illumination and observation of an object, comprising: a transparent window, wherein the transparent window is formed from an optical element and wherein the optical element includes at least one portion that provides for a magnified view of the object; and an adjustable light source coupled to the transparent window, wherein an output of the light source is adjustable relative to the transparent window.

2. The object viewer of claim 1, wherein the output of the adjustable light source is reflected off the transparent window to illuminate the object.

3. The object viewer of claim 1, wherein the adjustable light source is indirectly coupled to the transparent window.

4. The object viewer of claim 1, further comprising at least one of a multiplexer and a splitter for dividing the output of the adjustable light source into two portions for illumination of the object from a plurality of directions or angles.

5. The object viewer of claim 1, wherein the adjustable light source is a first adjustable light source and further comprising a second light source.

6. The object viewer of claim 5, wherein the second light source is a second adjustable light source.

7. The object viewer of claim 5, wherein the first adjustable light source provides a directed beam of light for illumination of the object and the second light source provides a beam of dispersive light for illumination of the object.

8. The object viewer of claim 5, wherein the first adjustable light source provides a beam of light in the visible spectrum and the second light source provides a beam of light in the non-visible spectrum.

9. The object viewer of claim 1, wherein the illumination of the object is part direct illumination and part reflective illumination.

10. The object viewer of claim 1, wherein the adjustable light source generates at least one of white light, tuned light, and light in the non-visible spectrum.

11. The object viewer of claim 1, wherein the adjustable light source is a tunable light generator.

12. The object viewer of claim 1, wherein the adjustable light source is positioned such that the output of the adjustable light source is dispersed substantially evenly onto the object.

13. The object viewer of claim 1, wherein the optical element is a holographic optical element.

14. The object viewer of claim 1, wherein the optical element is a lens.

15. The object viewer of claim 1, wherein the optical element includes an optical filter.

16. The object viewer of claim 15, wherein the optical element includes a front surface and a rear surface and wherein the optical filter prevents UV light from traveling through the optical element in the direction from the rear surface of the optical element to the front surface of the optical element.

17. The object viewer of claim 1, wherein the optical element is curved.

18. The object viewer of claim 1, wherein the adjustable light source provides for spot illumination.

19. The object viewer of claim 1, wherein the optical element includes a first portion that provides for a magnified view of the object and a second portion that provides for an unmagnified view of the object.

20. A method for providing illumination and viewing of an object, comprising: at least one of placing the object adjacent a transparent window and placing the transparent window adjacent the object, wherein the transparent window includes a portion that provides magnification; generating an output from a light source; and directing the output from the light source to the object; and adjusting the output from the light source relative to transparent window.

* * * * *